United States Patent
Qiu et al.

(10) Patent No.: US 11,452,493 B2
(45) Date of Patent: Sep. 27, 2022

(54) BIMODAL THREE-DIMENSIONAL MAMMARY GLAND IMAGING QUALITY DETECTING PHANTOM AND METHOD

(71) Applicant: TAISHAN MEDICAL UNIVERSITY, Shandong (CN)

(72) Inventors: Jianfeng Qiu, Taian (CN); Guozhu Wang, Taian (CN); Kun Hou, Taian (CN); Minghui Li, Taian (CN); Xueqian Yang, Taian (CN); Liting Shi, Taian (CN); Weizhao Lu, Taian (CN)

(73) Assignee: TAISHAN MEDICAL UNIVERSITY, Taian (CN)

( * ) Notice: Subject to any disclaimer, the term of this patent is extended or adjusted under 35 U.S.C. 154(b) by 981 days.

(21) Appl. No.: 16/304,097

(22) PCT Filed: Jun. 14, 2017

(86) PCT No.: PCT/CN2017/088168
§ 371 (c)(1),
(2) Date: Nov. 21, 2018

(87) PCT Pub. No.: WO2018/103290
PCT Pub. Date: Jun. 14, 2018

(65) Prior Publication Data
US 2019/0388054 A1    Dec. 26, 2019

(30) Foreign Application Priority Data
Dec. 9, 2016   (CN) .......................... 201611130359.6

(51) Int. Cl.
*A61B 6/00*    (2006.01)
*A61B 5/00*    (2006.01)
(Continued)

(52) U.S. Cl.
CPC ............ *A61B 6/583* (2013.01); *A61B 5/0035* (2013.01); *A61B 5/055* (2013.01); *A61B 6/502* (2013.01); *G01R 33/58* (2013.01); *G09B 23/286* (2013.01)

(58) Field of Classification Search
CPC ....... A61B 6/583; A61B 5/0035; A61B 5/055; A61B 6/502; G01R 33/58; G09B 23/286
See application file for complete search history.

(56) References Cited

U.S. PATENT DOCUMENTS

2004/0067591 A1* 4/2004 Madsen ................. A61B 8/485
                                                           600/437

FOREIGN PATENT DOCUMENTS

| CN | 103479369 A | 1/2014 |
|---|---|---|
| CN | 105949690 A | 9/2016 |

(Continued)

OTHER PUBLICATIONS

Sep. 14, 2017 International Search Report issued in International Patent Application No. PCT/CN2017/088168.
(Continued)

*Primary Examiner* — David P Porta
*Assistant Examiner* — Fani Polyzos Boosalis
(74) *Attorney, Agent, or Firm* — Oliff PLC

(57) ABSTRACT

A bimodal three-dimensional mammary gland imaging quality detecting phantom and method, which includes: a three-dimensional breast appearance phantom structure made of agarose gel containing polyethylene, which is a radiation equivalent material of adipose tissues under X-rays, the relaxation time of hydrogen protons in the agarose gel under a 3T magnetic field is equivalent to that of human adipose tissues, and mammary gland tissue duct phantoms and phantoms of lobules of mammary gland are distributed in the breast appearance phantom structure. The phantom can
(Continued)

be used for the image quality detection and analysis of mammary gland imaging by the systems of magnetic resonance and mammography, the material is elastic and can be compressed on a mammography platform for imaging, and the phantom can also be vertically placed in the magnetic resonance mammary gland coil for tomography, so two imaging modes of one phantom are achieved, and the application range is expanded.

14 Claims, 2 Drawing Sheets

(51) Int. Cl.
*A61B 5/055* (2006.01)
*G01R 33/58* (2006.01)
*G09B 23/28* (2006.01)

(56) References Cited

FOREIGN PATENT DOCUMENTS

| CN | 106491213 A | 3/2017 | |
|---|---|---|---|
| KR | 10-1026833 B1 | 4/2011 | |
| WO | 2008/021720 A2 | 2/2008 | |
| WO | WO-2008021720 A2 * | 2/2008 | ............. G09B 23/30 |

OTHER PUBLICATIONS

Sep. 14, 2017 Written Opinion of the International Searching Authority issued in International Patent Application No. PCT/CN2017/088168.

* cited by examiner

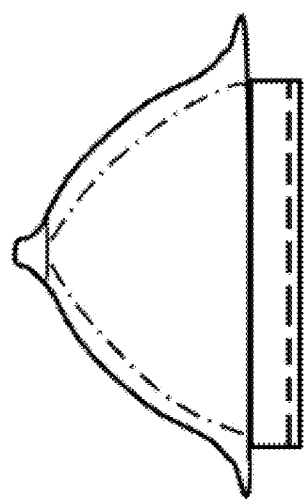
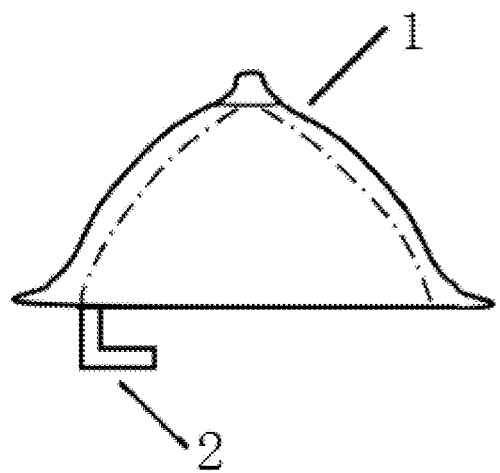
Fig.1    Fig.2
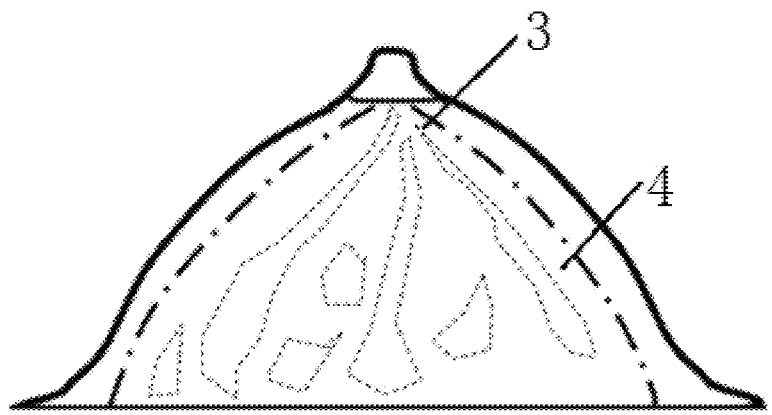
Fig.3
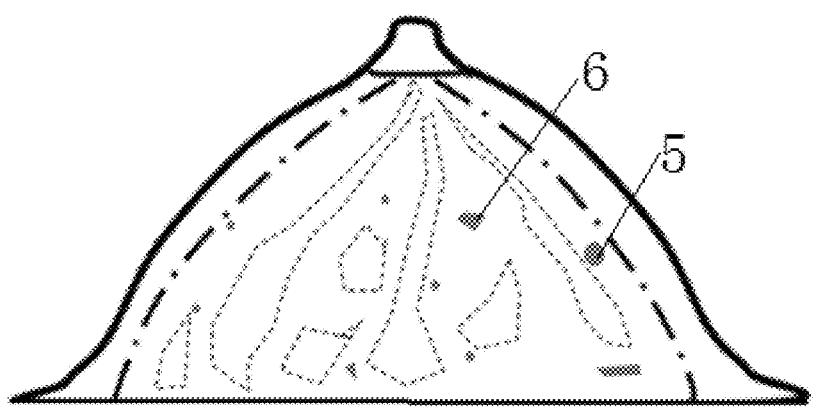
Fig.4

BIMODAL THREE-DIMENSIONAL MAMMARY GLAND IMAGING QUALITY DETECTING PHANTOM AND METHOD

FIELD OF THE INVENTION

The present invention relates to a mammary gland phantom, and in particular to a bimodal three-dimensional mammary gland imaging quality detecting phantom and method.

BACKGROUND OF THE INVENTION

Mammary gland diseases are high-risk diseases in women, which directly harm the health and life safety of the women. At present, the clinical conventional mammary gland imageological examination uses a digital mammary gland X-ray imaging system (x-ray mammography), during the imaging, the breast tissues need to be pressed and fixed by using a pressing plate and a supporting plate, and molybdenum target X-ray exposure imaging is performed. The x-ray mammogram is quick and easy to obtain, and is the main method for physical examination and mammary gland disease screening. However, due to the radiation imaging, there is a potential pathogenic risk. Therefore, magnetic resonance is gradually introduced into the mammary gland imaging and disease screening. A mammary gland coil is used in the magnetic resonance mammography, tomography is performed in a relaxed state of the mammary gland, and 3D stereoscopic image analysis can also be performed. The magnetic resonance mammography and molybdenum target X-ray imaging will play an important role in the mammary gland examination for a long period of time. Therefore, a detection phantom that can be used for both imaging modals are required for imaging quality detection and analysis, particularly for analyzing the sensitivity and specificity of the two different modal imaging methods for detecting mammary gland lesions, to propose a more reasonable examination solution and technical means.

SUMMARY OF THE INVENTION

The first objective of the present invention is to provide a bimodal three-dimensional mammary gland imaging quality detection phantom, wherein the phantom uses agarose gel to produce a breast appearance phantom structure, the gel contains a relaxation time value of hydrogen protons in glucolipid, and polyethylene is a radiation equivalent material of adipose tissues under X-rays, which can perform imaging under X-rays and can obtain a high-signal magnetic resonance image. The second objective of the present invention is to provide a mammary gland imaging method, which gives an imaging method of a phantom in two modes, and has practical guiding significance.

In order to achieve the above objective, the first technical solution provided by the present invention is as follows:

A bimodal three-dimensional mammary gland imaging quality detecting phantom includes a three-dimensional breast appearance phantom structure made of agarose high-density gel containing polyethylene therein, the polyethylene is a radiation equivalent material of adipose tissues under X-rays, the relaxation time of hydrogen protons in the agarose gel under a 3 T magnetic field is equivalent to that of human adipose tissues, mammary gland tissue duct phantoms and phantoms of lobules of mammary gland are distributed in the breast appearance phantom structure, the density of the agarose gel is 0.94 g/cm$^3$, and the mammary gland tissue duct phantoms and the phantoms of lobules of mammary gland are arranged according to the arrangement of actual mammary gland tissue ducts and lobules of mammary gland.

In the above-mentioned detection phantom, the breast appearance phantom structure simulates a breast structure in a natural relaxation state and is not pressed, thereby ensuring true and natural image quality, the material used has X-ray radiation tissue equivalence, magnetic resonance tissue equivalence (the relaxation value is similar to the relaxation value of the hydrogen nucleus in human body fat), the detection phantom can be used for two kinds of modal imaging, three-dimensional mammary gland appearance phantom structure can be used for tomography and image three-dimensional reconstruction. The phantom can be used for two kinds of imaging, thereby facilitating the imaging quality detection and analysis.

Mammary gland mass phantoms and calcified phantoms are further arranged in the breast appearance phantom structure, the mammary gland mass phantoms are made of nylon fibers, the calcified phantoms are made of calcium carbonate particles and are composed of 6 groups of calcium carbonate particles, the calcified phantoms are distributed in a three-dimensional space in the breast appearance phantom structure to simulate the lesion structure in the breast, which is convenient for imaging research.

The mammary gland mass phantoms is simulated by 4 groups of nylon fibers, which are composed of irregular shapes, and the area of each group is ≤2 cm$^2$; the calcified phantom is circular and has an area of 0.2-1 mm$^2$; and these sizes are clinical common size ranges of calcifications, thus ensuring morphological simulation of the lesion.

In order to ensure the simulation result of the breast structure, the mammary gland tissue duct phantoms are made of a resin material, and the phantoms of lobules of mammary gland are made of a liquid gel material containing bubbles.

The mammary gland tissue duct phantoms extend radially from a nipple to the rear of the breast appearance phantom structure in the breast appearance phantom structure and are distributed in a three-dimensional space.

A plurality of mammary gland tissue duct phantoms are provided, and the diameters of the plurality of mammary gland tissue duct phantoms are 2 mm, 1 mm, and 0.5 mm.

The phantoms of lobules of mammary gland are distributed in the breast appearance phantom structure in multiple groups.

In order to facilitate the fixation of the breast appearance phantom structure during the imaging, one side of the breast appearance phantom structure opposite to the nipple is provided with a fixing support for fixing the same to a pressing plate or arranging the same on the periphery of the mammary gland coil.

The fixing support is arranged in an L shape, and one end of the fixing support is fixed to the breast appearance phantom structure.

The second solution provided by the present invention is as follows:

A mammary gland imaging method includes: providing the bimodal three-dimensional mammary gland imaging quality detecting phantom;

fixing the breast appearance phantom structure by using a pressing plate, performing molybdenum target X-ray exposure imaging, fixing the breast appearance phantom structure on an imaging support plate by using the fixing support, and causing the pressing plate to naturally press the phantom from a semi-spherical shape into a semi-flat round shape, so that an internal simulation structure and lesions can both be subjected to X-ray imaging under the condition of tissue equivalence; and placing the breast appearance phantom structure in a coil area of magnetic resonance imaging, performing tomography with a thickness of ≥2 mm, and performing imaging.

The present invention has the following advantages:

1) By producing the three-dimensional breast appearance phantom structure via the agarose gel containing polyethylene therein, the imaging of the phantom structure under X-ray and the 3 T magnetic field is achieved, the imaging quality is good, and meanwhile, the real breast (mammary gland) tissues and lesions can be simulated.

2) The phantom can be used for the image quality detection and analysis of mammary gland imaging by the two imaging systems of magnetic resonance imaging and mammography, the material is elastic and can be compressed on a mammography platform for imaging, and the phantom can also be vertically placed in the magnetic resonance mammary gland coil for tomography, so that two imaging modes of one phantom are achieved, and the application range is expanded.

BRIEF DESCRIPTION OF THE DRAWINGS

FIG. 1 is a first schematic diagram of a phantom of the present invention;

FIG. 2 is a second schematic diagram of a phantom of the present invention;

FIG. 3 is a third schematic diagram of a phantom of the present invention;

FIG. 4 is a fourth schematic diagram of a phantom of the present invention;

Figure 5:
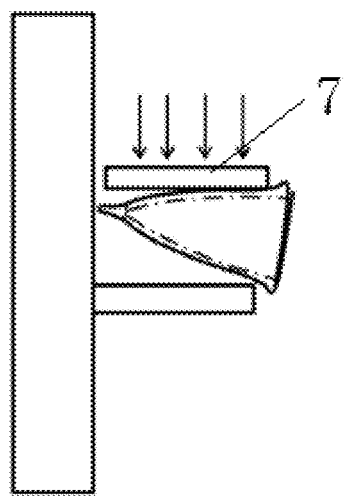
FIG. 5 is a schematic diagram of pressing of a phantom of the present invention during X-ray imaging.
Figure 6:
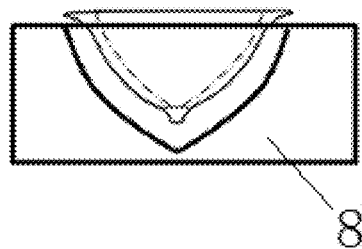
FIG. 6 is a schematic diagram of pressing of a phantom of the present invention during mammary gland coil imaging.

REFERENCE SIGNS 1 breast appearance phantom structure, 2 fixing support, 3 mammary gland tissue duct phantom, 4 phantom of lobules of mammary gland, 5 calcified phantom, 6 mammary gland mass phantom, 7 pressing plate, and 8 mammary gland imaging coil.

DETAILED DESCRIPTION OF THE EMBODIMENTS

The technical solutions in the embodiments of the present invention will be clearly and completely described below in combination with the drawings in the embodiments of the present invention.

The overall appearance of the breast appearance phantom structure 1 in the phantom is a semi-spherical shape with a diameter of 7 cm and a height of 10 cm, and the front segment contains a nipple structure, which simulates the outer appearance of the female breast in a natural state. A the bottom of the breast appearance phantom structure is provided with a PLA plastic fixing support 2, which is used for fixing the same to the pressing plate during the mammography and also for arranging the same on the periphery of the mammary gland coil during the mammary gland magnetic resonance imaging for fixing the phantom, as shown in FIG. 2.

The breast appearance phantom structure 1 is made of agarose high-density gel containing polyethylene, which is translucent, the density of polyethylene is 0.94 g/cm$^3$, the polyethylene is a radiation equivalent material of adipose tissues under X-rays at 40 kV, which is similar to the absorption coefficient of human body fat. The agarose high-density gel is rich in hydrogen protons, the $T_1$ and $T_2$ relaxation times in the 3 T magnetic field are equivalent to those of human body adipose tissues, which are similar to the relaxation times of human body fat and connective tissues. The agarose high-density gel is manufactured by the 3D printing (photosensitive resin molding) technology and has a uniform density throughout.

The agarose high-density gel of the phantom contains two simulated tissue structures, namely, mammary gland tissue duct phantoms 3 and phantoms 4 of lobules of mammary gland, which gradually converge from the bottom to the front of the phantom. The distribution morphology and spatial density simulate the real human body mammary gland structure. The mammary gland tissue duct phantoms 3 are made of a resin material and radially extend into the rear of the phantom from the nipple and are distributed in a three-dimensional space, and the mammary gland tissue duct phantoms 3 have three levels of sizes, and the diameters are respectively 2 mm, 1 mm and 0.5 mm. The phantoms 4 of lobules of mammary gland are made of a liquid gel material containing bubbles and are located at the bottoms of the mammary gland tissue duct phantoms and the rear of the phantom, the gel is hydroxyethyl cellulose, the phantom contains 15 groups of phantoms of lobules of mammary gland, the phantoms 4 of lobules of mammary gland are distributed in a three-dimensional space, each group takes the shape of an oval and has a volume of about 3 cm$^3$, as shown in FIG. 3. The specific production process of the bubble-containing gel is as follows: in a gel cooling process, performing the inflation pressurization and appropriate stirring to evenly distribute the bubbles in the gel with a certain range.

The phantom gel contains two simulated lesion structures, namely, mammary gland mass phantoms 6 and calcified phantoms 5, which are uniformly distributed in the breast appearance phantom structure 1. The mammary gland mass phantom 6 is simulated by 6 groups of nylon fibers and is composed of irregular shapes, and the area of each group is ≤2 cm$^2$. The calcified phantoms 5 are composed of 6 groups of calcium carbonate particles, are circular and have an area of 0.2-1 mm$^2$. The mammary gland mass phantoms 6 and calcified phantoms 5 simulate the lesions and are distributed in a three-dimensional space, as shown in FIG. 4.

The breast appearance phantom structure 1 can be compressed within 0.5 time of volume due to the use of the highly elastic gel, and the internal tissue and the diseased structure are unchanged after compression. The phantom can be placed in the imaging area during the mammography and is fixed on the imaging support plate, and the pressing plate naturally presses the phantom, the breast appearance phantom structure 1 is compressed from a semi-spherical shape into a semi-circular shape, and the X-ray imaging can be performed on an internal simulation structure and lesions under the condition of tissue equivalence, as shown in FIG. 5.

As the agarose gel containing the polyethylene in the breast appearance phantom structure 1 contains the relaxation time value of hydrogen protons in the glucolipid, high-signal $T_1$ and $T_2$ images can be obtained during the magnetic resonance imaging. During the imaging, the phantom is placed in the mammary gland imaging coil, the fixing support of the phantom can be fixed at the outside of the coil, so that the phantom is placed in the semicircular area of the coil in a natural state. Tomography (transverse, sagittal, and coronal scanning) with a thickness ≥2 mm can be performed by using a conventional imaging sequence. Magnetic resonance imaging can be performed on the internal simulation structure and the lesions under the condition of tissue equivalence. In addition, multi-plane reconstruction and surface rendering 3D reconstruction can be performed based on continuous tomography images.

Sources of the materials:

| Name | Raw material | Source |
| --- | --- | --- |
| Polyethylene | LLDPE(existing low-density polyethylene material) | LINGS company |
| Agarose Gel | Agarose reagent Polymer water gel forming agent | Originally imported from Spain America |
| Nylon fiber | Fiber nylon board | DuPont |
| Calcium carbonate particles | Calcium carbonate reagent | Hexagonal rhombohedral crystal calcite, Xilong Chemical |

Described above are merely preferred embodiment of the present invention, and it should be noted that those of ordinary skill in the art can also make a number of improvements and modifications without departing from the principles of the present invention, and these improvements and modifications should be encompassed within the scope of protection of the present invention.

The invention claimed is:

1. A bimodal three-dimensional mammary gland imaging quality detecting phantom, comprising a three-dimensional breast appearance phantom structure made of agarose gel containing polyethylene therein, wherein the polyethylene is a radiation equivalent material of adipose tissues under X-rays, the relaxation time of hydrogen protons in the agarose gel under a 3T magnetic field is equivalent to that of human adipose tissues, and mammary gland tissue duct phantoms and phantoms of lobules of mammary gland are distributed in the breast appearance phantom structure;
   wherein the mammary gland tissue duct phantoms are made of a resin material, and the phantoms of lobules of mammary gland are made of a liquid gel material containing bubbles; and
   wherein a plurality of mammary gland tissue duct phantoms are provided, and the diameters of the plurality of mammary gland tissue duct phantoms are 2 mm, 1 mm, and 0.5 mm.

2. The bimodal three-dimensional mammary gland imaging quality detecting phantom according to claim 1, wherein mammary gland mass phantoms and calcified phantoms are further arranged in the breast appearance phantom structure, the mammary gland mass phantoms are made of nylon fibers, and the calcified phantoms are made of calcium carbonate particles.

3. The bimodal three-dimensional mammary gland imaging quality detecting phantom according to claim 2, wherein the area of the mammary gland mass phantom is ≤2 $cm^2$; and the calcified phantom is circular and has an area of 0.2-1 $mm^2$.

4. A mammary gland imaging method, comprising:
   providing the bimodal three-dimensional mammary gland imaging quality detecting phantom according to claim 3;
   fixing the breast appearance phantom structure by using a pressing plate, and performing molybdenum target X-ray exposure imaging; and
   placing the breast appearance phantom structure in a coil area of magnetic resonance imaging, performing tomography with a thickness of ≥2 mm, and performing imaging.

5. A mammary gland imaging method, comprising:
   providing the bimodal three-dimensional mammary gland imaging quality detecting phantom according to claim 2;
   fixing the breast appearance phantom structure by using a pressing plate, and performing molybdenum target X-ray exposure imaging; and
   placing the breast appearance phantom structure in a coil area of magnetic resonance imaging, performing tomography with a thickness of ≥2 mm, and performing imaging.

6. The bimodal three-dimensional mammary gland imaging quality detecting phantom according to claim 1, wherein the mammary gland tissue duct phantoms extend radially from a nipple to the rear of the breast appearance phantom structure in the breast appearance phantom structure and are distributed in a three-dimensional space.

7. A mammary gland imaging method, comprising:
   providing the bimodal three-dimensional mammary gland imaging quality detecting phantom according to claim 6;
   fixing the breast appearance phantom structure by using a pressing plate, and performing molybdenum target X-ray exposure imaging; and
   placing the breast appearance phantom structure in a coil area of magnetic resonance imaging, performing tomography with a thickness of ≥2 mm, and performing imaging.

8. The bimodal three-dimensional mammary gland imaging quality detecting phantom according to claim 1, wherein the phantoms of lobules of mammary gland are distributed in the breast appearance phantom structure in multiple groups.

9. A mammary gland imaging method, comprising:
   providing the bimodal three-dimensional mammary gland imaging quality detecting phantom according to claim 8;
   fixing the breast appearance phantom structure by using a pressing plate, and performing molybdenum target X-ray exposure imaging; and
   placing the breast appearance phantom structure in a coil area of magnetic resonance imaging, performing tomography with a thickness of ≥2 mm, and performing imaging.

10. The bimodal three-dimensional mammary gland imaging quality detecting phantom according to claim 1, wherein one side of the breast appearance phantom structure opposite to the nipple is provided with a fixing support for fixing the same to a pressing plate or arranging the same on the periphery of the mammary gland coil.

11. A mammary gland imaging method, comprising:
   providing the bimodal three-dimensional mammary gland imaging quality detecting phantom according to claim 10;
   fixing the breast appearance phantom structure by using a pressing plate, and performing molybdenum target X-ray exposure imaging; and
   placing the breast appearance phantom structure in a coil area of magnetic resonance imaging, performing tomography with a thickness of >2 mm, and performing imaging.

12. A mammary gland imaging method, comprising:
providing the bimodal three-dimensional mammary gland imaging quality detecting phantom according to claim 1;
fixing the breast appearance phantom structure by using a pressing plate, and performing molybdenum target X-ray exposure imaging; and
placing the breast appearance phantom structure in a coil area of magnetic resonance imaging, performing tomography with a thickness of ≥2 mm, and performing imaging.

13. A bimodal three-dimensional mammary gland imaging quality detecting phantom, comprising a three-dimensional breast appearance phantom structure made of agarose gel containing polyethylene therein, wherein the polyethylene is a radiation equivalent material of adipose tissues under X-rays, the relaxation time of hydrogen protons in the agarose gel under a 3T magnetic field is equivalent to that of human adipose tissues, and mammary gland tissue duct phantoms and phantoms of lobules of mammary gland are distributed in the breast appearance phantom structure, wherein one side of the breast appearance phantom structure opposite to the nipple is provided with a fixing support for fixing the same to a pressing plate or arranging the same on the periphery of the mammary gland coil, and
wherein the fixing support is arranged in an L shape, and one end of the fixing support is fixed to the breast appearance phantom structure.

14. A mammary gland imaging method, comprising:
providing the bimodal three-dimensional mammary gland imaging quality detecting phantom according to claim 13;
fixing the breast appearance phantom structure by using a pressing plate, and performing molybdenum target X-ray exposure imaging; and
placing the breast appearance phantom structure in a coil area of magnetic resonance imaging, performing tomography with a thickness of ≥2 mm, and performing imaging.

* * * * *